US007065393B2

(12) United States Patent
Sati et al.

(10) Patent No.: US 7,065,393 B2
(45) Date of Patent: Jun. 20, 2006

(54) APPARATUS, SYSTEM AND METHOD OF CALIBRATING MEDICAL IMAGING SYSTEMS

(75) Inventors: Marwan Sati, Mississauga (CA); Martin Cyr, Longueuil (CA)

(73) Assignee: Cedara Software Corp., Mississauga (CA)

( * ) Notice: Subject to any disclaimer, the term of this patent is extended or adjusted under 35 U.S.C. 154(b) by 329 days.

(21) Appl. No.: 10/195,002

(22) Filed: Jul. 11, 2002

(65) Prior Publication Data

US 2004/0015077 A1    Jan. 22, 2004

(51) Int. Cl.
    *A61B 5/05* (2006.01)
(52) U.S. Cl. ............... 600/407; 600/425; 600/426; 600/427; 600/439; 378/4; 378/37; 378/40; 378/87; 378/197; 378/207
(58) Field of Classification Search ............... 378/207, 378/40, 197, 37, 87, 4; 345/647; 600/407, 600/439, 426, 425, 173, 427
    See application file for complete search history.

(56) References Cited

U.S. PATENT DOCUMENTS

| 5,072,733 | A | * | 12/1991 | Spector et al. ............ 600/439 |
| 5,267,293 | A | * | 11/1993 | Virta ....................... 378/40 |
| 5,289,520 | A | * | 2/1994 | Pellegrino et al. ........ 378/37 |
| 5,426,685 | A | * | 6/1995 | Pellegrino et al. ........ 378/87 |
| 5,772,594 | A | * | 6/1998 | Barrick ................... 600/407 |
| 6,379,043 | B1 | * | 4/2002 | Zylka et al. .............. 378/207 |
| 6,484,049 | B1 | * | 11/2002 | Seeley et al. ............. 600/426 |
| 6,490,475 | B1 | * | 12/2002 | Seeley et al. ............. 600/426 |
| 6,504,892 | B1 | * | 1/2003 | Ning ....................... 378/4 |
| 6,739,752 | B1 | * | 5/2004 | Sabczynski et al. ...... 378/207 |
| 2002/0109705 | A1 | * | 8/2002 | Hofstetter et al. ........ 345/647 |
| 2004/0208289 | A1 | * | 10/2004 | Barta et al. .............. 378/197 |

FOREIGN PATENT DOCUMENTS

| WO | 99/23452 | 5/1999 |
| WO | WO 00/66971 | 11/2000 |

OTHER PUBLICATIONS

Fahrig R et al: "Three-dimensional computed tomographic reconstruction using a C-arm mounted XRII: Image-based correction of gantry motion nonidealities" Medical Physics, Jan. 2000, AIP for American Assoc. Phys. Med, USA, vol. 27, No. 1, pp. 30-38, XP002262718 ISSN: 0094-2405 section "Conclusion".

* cited by examiner

*Primary Examiner*—Brian L. Casler
*Assistant Examiner*—Baisakhi Roy
(74) *Attorney, Agent, or Firm*—Pearne & Gordon LLP (57) ABSTRACT

A C-arm imaging device method, apparatus and system are provided. The apparatus and system includes a module for determining the positions of an imaging source and an imaging receptor and a local gravity vector to determine an imaging source focal point displacement. The apparatus and system may include a module for determining magnetic field distortion. Data obtained by the apparatus and system can be stored for use in subsequent interpolation of imaging source focal point displacement for the C-arm imaging device.

30 Claims, 4 Drawing Sheets

APPARATUS, SYSTEM AND METHOD OF CALIBRATING MEDICAL IMAGING SYSTEMS

FIELD OF THE INVENTION

The present invention relates to medical imaging systems, and is particularly concerned with an apparatus, system and method for calibrating medical imaging systems used in computer-assisted surgery.

BACKGROUND OF THE INVENTION

Minimally invasive, surgical techniques are becoming more prevalent as a means to reduce injury to the patient during surgical procedures, and thereby improving patient recovery to this ted, computer assisted surgical (CAS) techniques are being employed more frequently.

In conventional CAS, surgeons employ computational and image processing technologies to assist in surgical procedure. High resolution, three-dimensional internal images of a patient are taken prior to surgery, for example, computerized tomograph (CT) or magnetic resonance imaging (MRI). The images are digitized, processed and saved in a computer system for use in a variety of purposes. In this specification, CAS includes surgical planning, surgical navigation, image guided surgery, and the like.

For example, before surgery, the saved images are registered to the patient. During surgical procedure, the intra-operative position of surgical instruments connected to a CAS system may be tracked by positioning sensors. The position of tracked surgical instruments in space is computed and the information merged with the saved images of the patient. The computer displays the position of surgical instruments corresponding to the saved images of the patient. The images displayed are then updated in accordance with the positioning of tracked surgical instruments to provide the surgeon with a real-time view of she surgical instruments and the surgical site.

More recently, an intra-operative imaging modality incorporated into CAS for orthopedic surgical procedure and navigation is fluoroscopy. Fluoroscopy utilizes X-ray radiation to obtain pre-operative internal images.

Generally, fluoroscopy utilizes a C-arm x-ray imaging device. A typical C-arm imaging device consists of a C-arm attached to a base with an X-ray source at one end of the C-arm and an image intensifier on the other end. The X-ray source emits X-rays, which are passed through a patient's body. On the other side of the C-arm, the image intensifier detects the X-rays and converts the received photons into a video signal of a two-dimensional image. By taking multiple two-dimensional images from multiple perspectives, a three-dimensional image can be derived. To change the image perspective, the C-arm is rotated to multiple positions and X-ray radiation passed through the interested portion of the patient's body at various angles.

However, initial images generated exhibit distortion due to a number of sources. One source of distortion is gravity. As the C-arm is rotated about the measuring field, the force of gravity deforms the C-arm, resulting in a change in the distance between the X-ray source and the image intensifier. Such deformations vary with changes in the orientation of the C-arm, resulting in radial and rotational distortions of the image produced by the image intensifier.

Another source of distortion is the Earth's magnetic field. The Earth's magnetic field varies continuously. Changes in the magnetic field affects electron velocity in an image intensifier producing rotational distortion of the image that varies non-linearly in the radial direction.

Before the saved image may be employed for CAS, including image-guided surgery and surgical navigation, the system must compute substantially all distortion to allow the positioning information to be accurately overlaid on the saved image.

A calibration process is needed to characterise the C-arm to remove image distortion and to define a mathematical projection model that will allow the projection of tracked surgical instruments in the fluoroscopic images.

Currently existing C-arm calibration techniques use either one or two calibration plates provided adjacent to the image intensifier. The plates contain radio-opaque beads spaced in a well-defined geometry in one or more planes, and are positioned in the path of the X-rays. The beads are visible in the captured images. All systems have at least one grid plate mounted just above the X-ray receptor plate. This grid is often termed the "dewarp grid" since it serves to unwarp the image of both magnetic distortions and other artefacts of the image amplification process. The amount of distortion for each point in the image can be determined, because the true relative position of the beads in the initial images is known. The computer system can compute and then digitally compensate for distortion and generate a substantially distortion-free image.

Most systems have a second grid termed the "projection grid". The projection grid lets the system calculate the X-ray projection lines and position of the X-ray source. The systems track the relative position of the C-arm intensifier and the surgical tools. Knowing the 3D position of the fiducial beads of the grid(s) and their 2D projections allows the system to calculate instrument position on each acquired image. The dewarp grid and the projection plate are each typically housed in plates that are termed the "calibration plate(s)".

However in these systems, calibration plate(s) need to remain on the C-arm throughout the entire surgical procedure. The presence of the projection grid plate decreases the available space between the image intensifier and the X-ray source in which to position a patient, an operating table and instrumentation, and, as well, to conduct surgical procedure. The presence of fiducial beads in the image also degrades the image quality. As such, it is desirable to use a C-arm with only one dewarp grid, or more advantageously, without having to use any grids at all.

The main disadvantage associated with the use of a single dewarp grid, is the lack of information relating to C-arm deformation due to gravity-induced bending. This information is required to compete the C-arm source position.

PCT/CH97/00418 filed Nov. 4, 1997, and published May 14, 1999, Hofstetter, R. et al., discloses an optically tracked body aligned with the local gravitational field suspended from a stationary object in a operating room. The body's spatial coordinates are determined using position sensors in the room. A plotting unit, also in the room, determines a system of coordinates, one of whose axes corresponds with the orientation in the local gravitational field, which can be used as a reference system for use in computer-assisted surgery and navigation, and during image-guided surgery. A limitation associated with this method is that the suspended body must not move throughout the surgical procedure. If the suspended body or the positioning sensor moves, the calibration process needs to be repeated, which may cause some difficulty if calibration is required during a surgical procedure. Another limitation is that the sensor must be placed so that it can be men which is cumbersome during surgery.

Another method of calibration involves the use of encoders on a position sensor stand to relate position measurements to gravity, defined by the base of the stand. The encoders are calibrated in optical tracking space to obtain a gravity reference, which can be later used in image guided surgery and surgical navigation procedures. Limitations associated with this method include the necessity of encoding, of position sensors, the complexity of calibrating encoders and optical position sensors and the assumption that the position sensor base is oriented consistently with gravity.

Further, this method requires a dewarp grid. Without a dewarp grid, there is insufficient information to compute and correct for magnetic field induced distortions in the image.

SUMMARY OF THE INVENTION

The present invention seeks to provide a method, system and apparatus for calibrating medical imaging systems that minimizes the above problems.

In accordance with an aspect of the present invention there is provided a method of calibrating at C-arm imaging device which includes the steps of determining a position of an imaging source, position of an imaging receptor, and a local gravity vector for each of a plurality of orientations of the C-arm. Imaging source focal point displacement due to bending is determined using the position of the imaging source and the position of the imaging detector in correspondence to he local gravity vector for each of the plurality of orientations. The above information is stored for use in subsequent interpolation of imaging source focal point displacement based on a specific position of an imaging receptor a specific local gravity vector.

In one embodiment of the invention, a C-arm image apparatus is precalibrated by deriving a look up table comprising information on the position of the imaging source, the position of the imaging receptor, the position of the image receptor with reference to the local gravitational field, and focal point displacement of the imaging source due to C-arm bending due to gravity, for each of a number of orientations of the C-arm upon orbital and lateral rotation.

In another embodiment of the invention, a C-arm image apparatus is precalibrated by deriving a look up table that additionally includes a determination of magnetic field distortion for each of a number of orientations of the C-arm upon orbital and lateral rotation.

In other aspects of the present invention, a C-arm imaging device and a system are provided with position determination means for determining the position of an imaging source and an imaging apparatus, and means for determining a local gravity vector. Imaging source focal point displacement due to bending determination means and information storage means are also provided.

In a further embodiment, the C-arm imaging apparatus is further provided with a magnetic pole sensor on a support base.

The calibration procedure is not required before each surgery, but can be pre-operatively conducted periodically.

Further, by providing the C-arm with a gravity sensor, a calibration plate at a distance from the image intensifier is no longer required. By providing direct angle measurements to the system through a gravity sensor, it is unnecessary to determine gravity references with respect to a position tracking system.

By the inclusion of a Magnetic North sensor, the distortion effects of the Earth's magnetic field on image creation can be modelled and distortion correced in the displayed images. The use of a magnetic north sensor in combination with the gravity sensor would dispense with the need for any calibration plates.

When the projection grid is removed, more space between the image intensifier and the X-ray source is created in which to fit the patient, and to perform surgical procedure, which is a strong clinical benefit. Removal of both calibration plates would not only increase the space between we image intensifier and the X-ray source, but would also result in an image unobscured by the radio-opaque beads on the calibration plates.

Such a system may be adapted for use with existing C-arm fluoroscopy devices.

BRIEF DESCRIPTION OF THE DRAWINGS

The present invention will be farther understood from the following description with references to the drawings in which:

FIG. 1b illustrates a view of the C-arm imaging apparatus of the embodiment of FIG. 1a;

DETAILED DESCRIPTION OF THE INVENTION

Figure 1A:
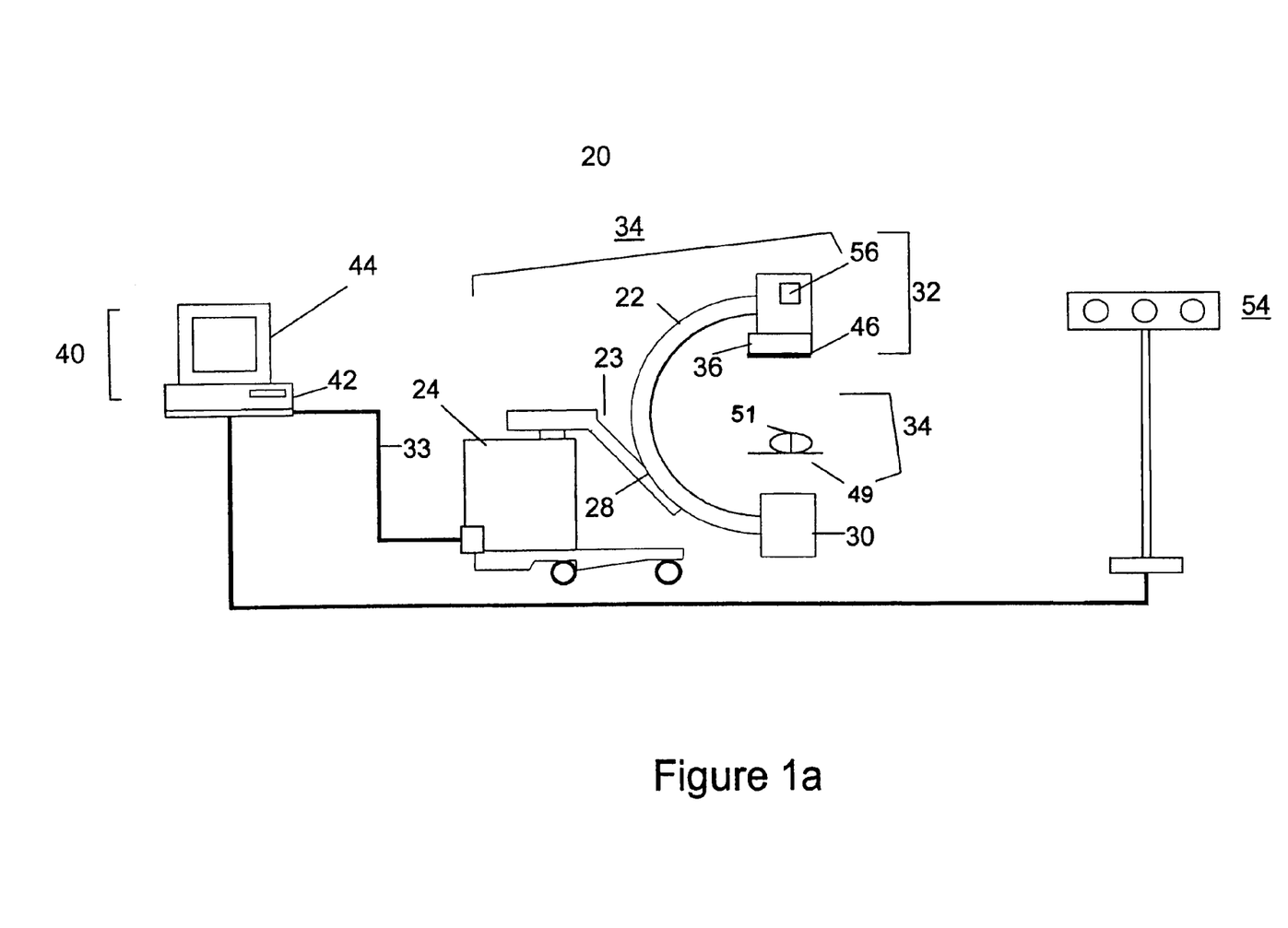
FIG. 1a illustrates a C-arm imaging apparatus and associated devices in accordance with an embodiment of the invention.
Figure 1B:
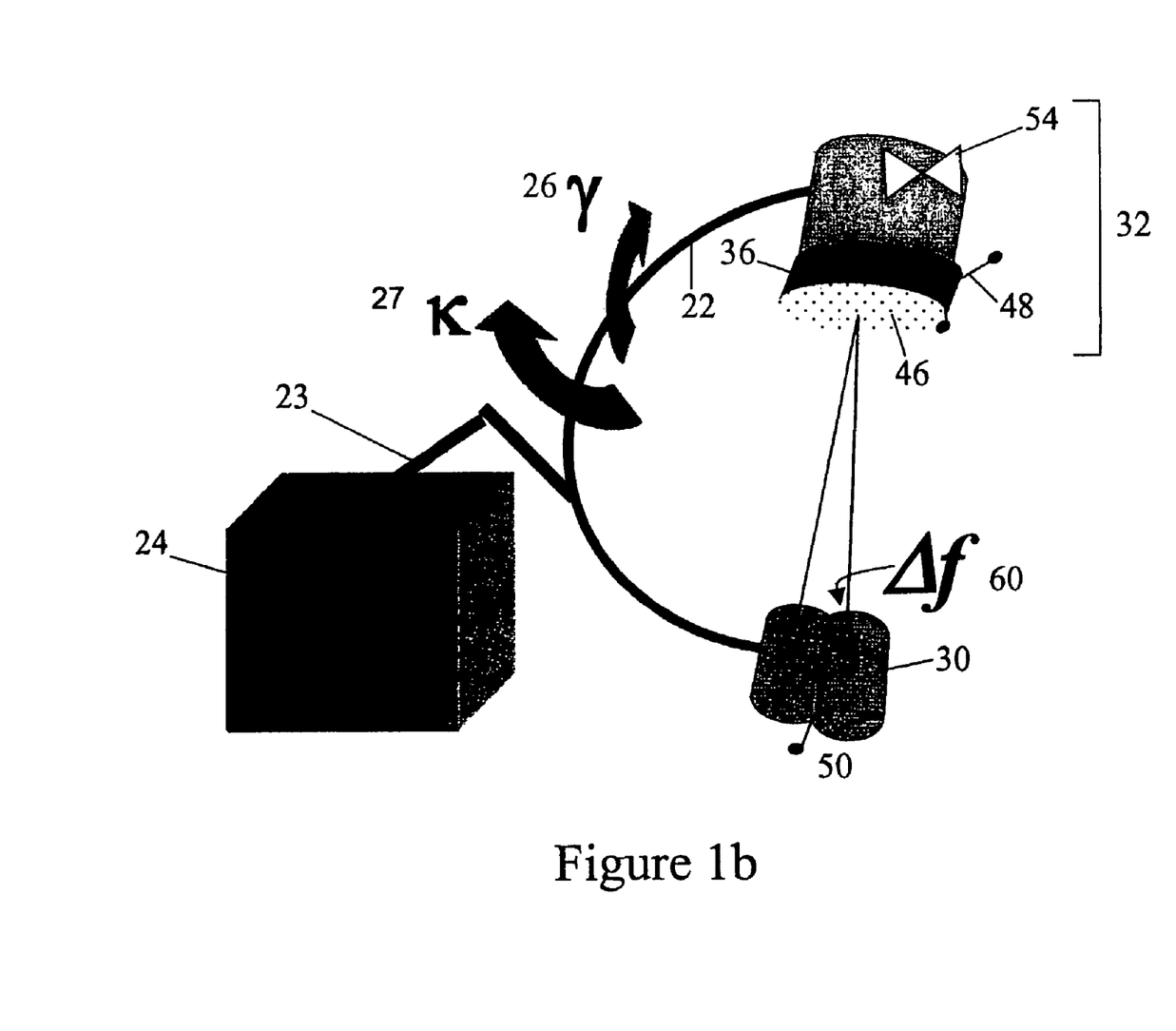

Referring to FIGS. 1a and 1b, a fluoroscopic C-arm X-ray imaging apparatus is provided. Imaging device 20 includes a C-arm 22 slidably and pivotally attached to a downwardly extending L-arm 23 at an attachment point 28. The L-arm 23 is held in suspension by a support base 24. The C-arm 22 is orbitable γ degrees about an axis of orbital rotation 27, while the L-arm 23 is rotatable κ degrees about an axis of lateral rotation 27 to thereby rotate the C-arm 22 laterally. The imaging device 20 may electronically communicate with a control unit (not shown) such that the control unit through external input may operate the degree of orbital and lateral rotation of the imaging device 20. The degrees of rotation γ and κ may be displayed for orientation.

An imaging source 30 is located at one end of C-arm 22 and imaging receptor 32 is located at the other end of C-arm 22. In the embodiment depicted in FIGS. 1a and 1b, the imaging source 30 is an X-ray source while the imaging receptor 32 is an assembly which includes an image intensifier 36. However, other imaging sources may be used. The C-arm 22, X-ray source 30 and X-ray receptor 32 are rotatable about, and define a free space 34 in which a C-arm table 49 and patient 51 may be positioned.

The X-ray source 30 comprises a high-voltage generator, and an X-ray tube (not shown) capable of generating continuous or pulsed stream of X-ray photons that passes through the free space 34 to the image receptor 32. A collimator (not shown) is also provided to collimate an X-ray stream to reduce the spread of unwanted radiations. In operation, electrons are accelerated through the X-ray tube by an electric field generated by the generator. When electrons strike the anode in the X-ray tube, X-rays are produced and emitted through the collimator and on through the free space 34.

The X-ray receptor 32 generates an image representing the intensities of received X-rays that have passed through the free space 34, including through all objects positioned therein, including a patient's body 51. In the embodiment, the described X-ray receptor 32 comprises an image intensifier 36 that converts the received X-ray photons to visible light. The image intensifier 36 is electronically coupled to a digital charge coupled device (CCD) camera (not shown) that converts the visible light to an analog video signal. The camera is interfaced to a computer workstation 40.

A computer workstation 40 includes a computer 42 with a graphics processor. The computer 42 is electronically interfaced with at least one video display monitor 44 or other display. The graphics processor may be a video capture and display circuit board such as Matrox Meteor-II™ that is capable of capturing, digitizing and displaying an analog video signal. The computer 42 is provided with a plurality of data input interfaces for the receipt, storage and processing of data received from external sources, as more particularly described below. Without limitation, input interfaces include electronic interfaces (for example port connections to external source devices, modems, keyboard, mouse, etc.), optical interfaces, or radio frequency interfaces.

The computer 42 is provided with sufficient memory, data storage, and processing speeds sufficient to process, store and display high quality, high volume video data. The computer may also be provided with a network card to interface with a network.

The computer 42 is further provided wit commercially available or custom designed software applications for CAS. The software applications include surgical navigation software, system calibration software, visualization software, image guidance software, and instrumentation software. The software applications may be established on a shared platform for the integration of multiple technologies and for efficient operability of the system.

The computer workstation 40 operates as a control centre to receive images from medical imaging devices and external data input, including medical instrumentation and user input. The computer workstation 40 further processes, stores and displays images, including raw, processed, manipulated, real-time or static, or integrated multiple images, as may be selected by a computer operator, for example, a surgical assistant.

In the embodiment of FIG. 1*a*, the image receptor 32 is further fitted with a calibration plate 46 containing one dewarp grid (not shown), which is clamped onto the image intensifier 36. The calibration plate 46 contains radio-opaque beads spaced in a well-defined geometry and is positioned adjacent to the image intensifier 36 and in the path of incoming X-ray photons emitted from the X-ray source 30. The raw, unprocessed images overlaid with the images of the radio-opaque beads as captured by the image intensifier 36 will appear distorted following X-ray transmission through the calibration plate 46. Information regarding the actual positioning of the radio-opaque beads previously stored in the computer 42 is used in a mathematical model to compute image distortion. The mathematical model is derived using conventional means and may be applied to process captured raw image for display in substantially distortion-free form. The mathematical model may be embodied in software such as navigation or imaging software applications.

In the embodiment depicted in FIG. 1*b*, one tracking shield 48 is attached to the image intensifier 36 and the second tracking shield 50 to the X-ray source 30. The positions of the tracking shields 48 and SO are precisely determined such that relative distance between the two tracking shields 48 and 50 can be computed and stored into the computer 42 for later use as will be described below. The tracking shields 48 and 50 serve as trackers for use with position sensors, which operate to define coordinates in three-dimensional space of the tracker. In the embodiment of FIG. 1*b*, the tracking shields 48 and 50 are provided with a plurality of active optical trackers with infrared light emitting diodes (IREDs) attached thereto. The trackers are electronically connected to a control unit of a position sensor system, which can control the firing of the IREDs. Alternatively, a plurality of individually attached IRED optical trackers may be manually attached to the image receptor assembly 32 and to the X-ray source 30.

A position sensor 54 is set a distance away from the imaging device 20, in unobstructed view of the various IREDs on the tracking shields. The position sensor 54 composes a processing unit connected with a computer interface card, which is inserted into the computer 42 on which instrumentation software for collecting and displaying data has been loaded. The position sensor 54 identifies the infrared light emitted from the IREDs and the processing unit computes the three-dimensional position of the trackers. The data is saved in the computer 42 for later use.

Alternatively, a passive optical sensor system may be used. A passive optical sensor uses reflective markers. The optical camera in a hybrid optical sensor system emits infrared signals, which are reflected back to the camera by the reflective marker. The position sensor 54 identifies the position of each marker, and using algorithms, reconstructs the three-dimensional coordinates of each marker in its processing unit. The position sensor 54 may be interfaced with the computer 42 for data communication of position in 3D coordinate space.

While optical sensors are preferred as position sensors, other position sensors may be used, including mechanical sensors comprising articulated arms with potentiometers at each joint, sonic sensors comprising the detection of the speed and direction of sound waves from positioned acoustic emitters, magnetic sensors, which detect phase and intensity of magnetic fields, and the like. Position sensors and trackers may be custom designed or commercially available Alternatively, trackers may be integrated into the imaging device 20.

A gravity sensor 56 is mounted on a mobile part of the C-arm 22, in this case, on the image intensifier 32. The gravity sensor 56 measures the orientation of the surface to which it is attached by measuring the direction of the gravitational force, and the inclination and roll angles, with reference to the directional gravitational force. Using this information, a gravity vector can be determined relative to the position in 3D space of the object on which the gravity sensor is mounted, in his case, the image intensifier 36. The gravity sensor 56 may have a digital output that is interfaced with tee computer 42 to transfer angulation data, which can be stored and subsequently used. The gravity sensor 56 may be custom-designed or commercially available, externally attachable to the imaging device 20. Alternatively, the gravity sensor 56 may be integrated to the imaging device 20 on manufacture. Alternatively, the angulation data may be manually inputted into an appropriate software application for subsequent use, for example, where the gravity sensor 56 displays angulation data, but lacks computer interface capability.

The calibration procedure for the imaging device 20 is performed as follows. Referring to FIGS. 1a and 1b, the imaging device 20 is orbitally rotated γ degrees 26 and laterally rotated κ degrees 27. The degrees of rotation may be, for example, electronically, mechanically or manually determined. The information may be directly transmitted to a computer workstation 40 via an interface or manually entered by an operator. The angulation values for γ and κ are recorded in a Look Up Table (LUT).

The LUT is a database contained in a custom-designed or commercially available software application. The LUT is adapted to register data, including data directly received through a computer interface or data manually recorded and entered by an operator via a keyboard, for later use with distortion correction mathematical models in CAS. In an embodiment, a single LUT may be used to compile sufficient distortion-correction data. Alternatively, other data collection means may be used, for example, multiple databases.

The imaging device 20 orientation is defined by the degree of rotation γ and κ. For the imaging device position $γ_1$ and $κ_1$, the gravity sensor 56 orientation on the C-arm 22 is determined with reference to angles α and β relative to and in alignment with the local Earth's gravitational field. A digital gravity sensor 56 transmits the angulation data to the computer workstation 42, and recorded in the LUT, corresponding to the C-arm position.

For the imaging device 20 position $γ_1$ and $κ_1$, the position sensor 54 determines the position of the optical trackers 48 and 50 on the image intensifier 36 and on the X-ray source 36. In the embodiment of FIG. 1a, the position of the tracking shield 48 on the image intensifier 36 is determined with reference to the three-dimensional position in space $x_1$, $y_1$, $z_1$. Similarly, the position of the tracking shield 50 on the X-ray source 30 is determined with reference to the three-dimensional position in space $x_2$, $y_2$, $z_2$. The position sensor 52 transfers positional data via its electronic interface to the computer workstation 40 for recording as various positional reference coordinates and for subsequent use in an appropriate LUT or alternative software application.

Referring to FIG. 1b, for the imaging device 20 position γ and κ, the $Δf_x$, $Δf_y$, $Δf_z$, are computed in order to obtain distortion variables defining C-arm bending. To determine the displacement of the C-arm X-ray source focal point due to bending (Δf) 60, a reference is obtained at position $γ_1=0$ and $κ_1=0$. The $x_{ref}$, $y_{ref}$, $z_{ref}$ positions of the two optical trackers mounted respectively on the image intensifier and source are determined and stored.

For subsequent orientations, $γ_s$ and $κ_s$, the $x_s$, $y_s$, $z_s$ coordinates of the tracking shield 50 on the X-ray source 30 are subtracted from the corresponding reference $x_{ref}$, $y_{ref}$, $z_{ref}$ to obtain $Δf_x$, $Δf_y$, $Δf_z$. The calculations to compute Δf for each of the x, y, and z spatial coordinates may be incorporated in the software application or separately performed manually.

The imaging device 20 is them rotated to another position $γ_2$ and $κ_2$, and the data relating to a, β, $Δf_x$, $Δf_y$, $Δf_z$ is determined and recorded on the LUT. A number of entries are recorded for a number of orientations of the C-arm, for example, ten γ by ten κ spaced at 10°. Preferably, at least 100 entries are obtained, for greater accuracy.

An example of a LUT as displayed on a computer display may appear as follows:

| γ | κ | α | β | $Δf_x$ | $Δf_y$ | $Δf_z$ |
|---|---|---|---|---|---|---|
| 0 | 0 | 0 | 0.13 | 0 | 0 | 0 |
| 10 | 0 | 10.3 | 0.45 | 0.7 | −1.2 | 0.2 |
| 20 | 0 | 20.5 | 0.33 | 2.4 | 1.8 | −0.9 |
| ... | ... | ... | ... | ... | ... | ... |
| 0 | 10 | 0.62 | 10.6 | 0.2 | 1.1 | 0.04 |
| 10 | 10 | 10.3 | 0.34 | 1.1 | −0.6 | 1.3 |
| 20 | 10 | 20.4 | 0.72 | 3.4 | −1.3 | 2.8 |
| ... | ... | ... | ... | ... | ... | ... |

The information contained in this look up table (LUT) may be stored in a surgical computer navigation system such as the SNN™ system for later use in CAS, including intra-operatively.

Figure 2:
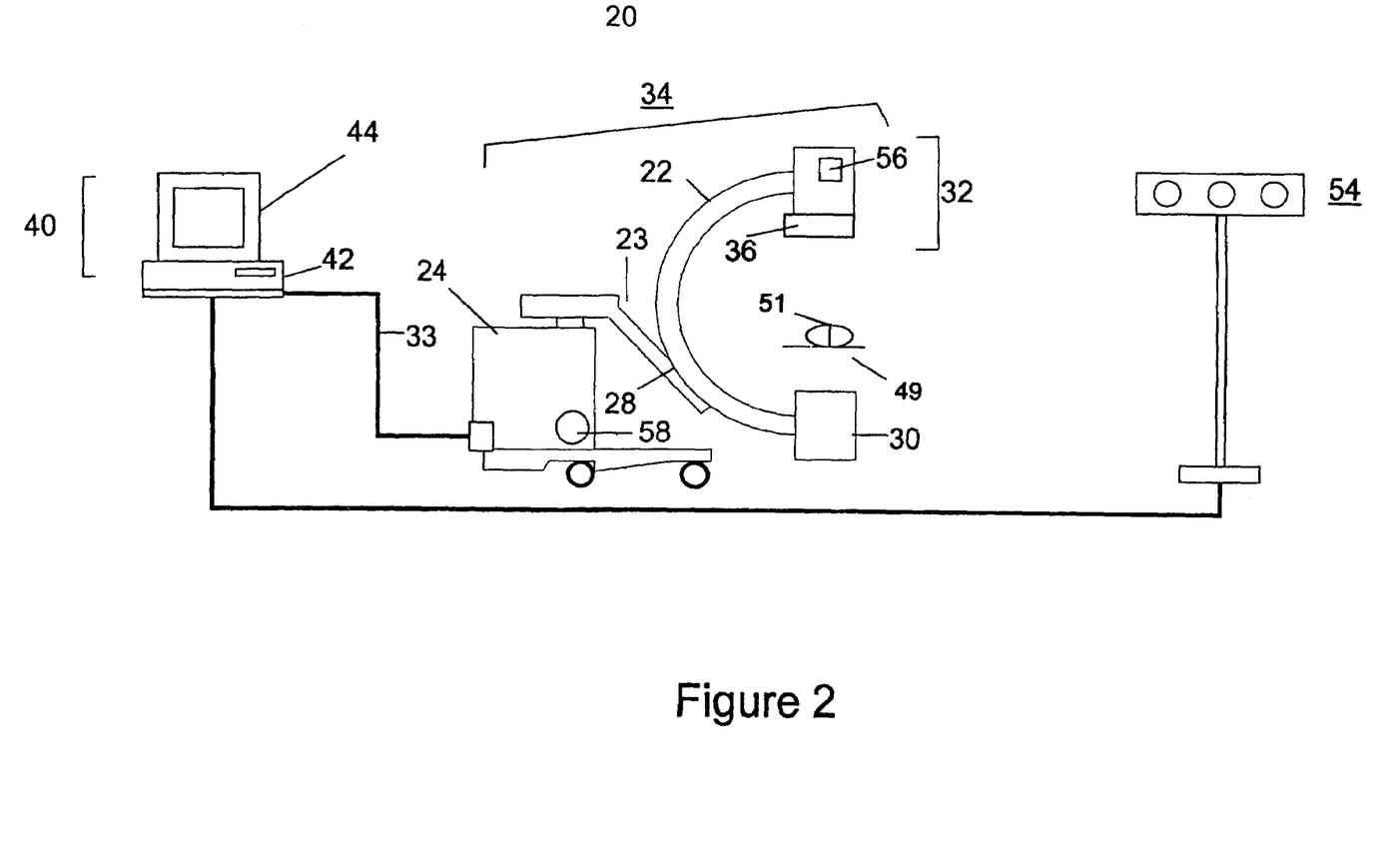
FIG. 2 illustrates C-arm imaging apparatus in accordance with another embodiment of the invention.

FIG. 2 depicts an imaging device 20 substantially similar to that of FIGS. 1a and 1b except lacking the calibration plate attached to the image intensifier 36 of FIGS. 1a and 1b. Also, a magnetic pole sensor, in this embodiment, a magnetic north sensor 58 is provided on the support base 24. In FIGS. 1 and 2, the same numerals denote the same structure to facilitate understanding of the Figures.

The magnetic north sensor 58 is a digital compass sensor that can accurately detect the Earth's magnetic north and is in orientation with the local magnetic field. The magnetic north sensor 58 can be directly interfaced with the computer 42 to communicate measured directional data, which can be saved, stored and subsequently used during computer-assisted surgery. Alternatively, angulation data may be manually inputted into an appropriate application for subsequent use, for example, where the magnetic north sensor is a fluid-based compass lacking interface ability. The magnetic north sensor 56 may be a custom-designed or commercially-available unit, externally attachable to the base of the imaging device 20. Alternatively, the magnetic north sensor 56 may be integrated into the imaging device 20 on manufacture.

In addition to the data measured for the data relating to a, β, $Δf_x$, $Δf_y$, $Δf_z$, with reference to a particular position of the imaging device 20 identified by angles γ and κ, readings from the magnetic north sensor 58 are also taken and recorded in the LUT as magnetic field directional reference coordinates. The magnetic north sensor 58 provides data to determine the local orientation of Earth's magnetic north. The magnetic north sensor displays directional data as an x, y, z vector. However, the vector may vary on distortion, for example, under the influence of magnetic fields, generated by operation of the X-ray source 30, the image receptor 32, an electrical current, or the like.

For the imaging device 20 position γ and κ, the $Δm_x$, $Δm_y$, $Δm_z$, are computed in order to obtain reference values to define the magnetic field distortion variables with respect to the magnetic field. The calculations to compute Δm for each of the x, y, and z spatial coordinates may be incorporated in the software application or performed manually separately.

In this case, Δm is the change in the magnetic field relative to a reference $m_{ref}$ at $γ_{ref}$, $κ_{ref}=0$. At a given angle $γ_1$, $κ_1$ of the C-arm, Δm is computed by subtracting the current $m_x$, $m_y$, $m_z$ coordinates from the reference $m_{xref}$, $m_{yref}$, $m_{zref}$ coordinates to yeild $Δm_x$, $Δm_y$, $Δm_z$.

An example of a LUT including magnetic north data, and magnetic field distortion data, as displayed on the computer display 44 may appear as follows:

| γ | κ | α | β | $\Delta f_x$ | $\Delta f_y$ | $\Delta f_z$ | Magnetic North Sensor | $\Delta m_x$ | $\Delta m_y$ | $\Delta m_z$ |
|---|---|---|---|---|---|---|---|---|---|---|
| 0 | 0 | 0 | 0.1 | 0 | 0 | 0 | 0 | 0 | 0 | 0 |
| 10 | 10 | 10.3 | 0.5 | 0.7 | −1.2 | 0.2 | 0 | 0 | 0.2 | 0.02 |
| 30 | 30 | 20.5 | 0.3 | 2.4 | 1.8 | −0.9 | 0 | 0 | 0.3 | 0.04 |
| ... | ... | ... | ... | ... | ... | ... | ... | ... | ... | ... |
| 0 | 10 | 0.62 | 11 | 0.2 | 1.1 | 0.04 | 10 | 0 | 0.3 | 0.13 |
| 10 | 10 | 10.3 | 20 | 1.1 | −0.6 | 1.3 | 20 | 0.1 | 0.1 | 0.03 |
| 20 | 10 | 20.4 | 31 | 3.4 | −1.3 | 2.8 | 30 | 0.3 | 0.2 | 0.1 |
| ... | ... | ... | ... | ... | ... | ... | ... | ... | ... | ... |

The information contained in this version of the LUT may be stored in a surgical computer navigation system such as the SNN™ system for later use in CAS, including intra-operatively.

Imaging device 20 calibrated in the manner set out above may be subsequently used in surgical navigation, image guided surgery or other CAS procedure.

As an example, the imaging device 20 as depicted in FIG. 1*a* is subsequently used in image-guided surgery. Optionally, the tracking shield 50 on the X-ray source 30 may be removed prior to intra-operative use as it is not longer required in subsequent, including intra-operative, procedure. As a further alternative, the image receptor assembly 32 may be additionally provided with an X-ray off detector (not shown) to detect when a new image has been inquired. For example, the X-ray detector may be in the form of a detector diode that directly absorbs received X-ray radiation or a photodiode with a scintillator. The X-ray off detector way be used to synchronize the fluoroscopic image with the optical position tracking data. The X-ray off signal can also be obtained directly from the C-arm console if such a synchronisation interface is available.

Surgical or other intra-operative instrumentation and tools may be used in conjunction with a CAS. Such tools, which include probes, pointers, wands, drill guides, awls, suction units with inserts, reference clamps and pins, may be provided with integrated tracking, where tracking technology is embedded in the tool, or mounted with one or more removable trackers, and can be localized in space (tracked) by a position sensor.

As an example, optically tracked tools may be used in conjunction with the embodiment of FIG. 1*a*. A sample integrated probe comprises a handle to which active optical IRED trackers are attached and a probe tip. The active optical tracker is interfaced with the control unit of the position sensor system, for example, an optical camera system. The system controls the firing of the IRED on the handle of the probe. The system determines the position of the probe in the operating room. The positioning information may be interfaced into the computer workstation 42 for image processing and display. The probe's geometry, instrument type and image is programmed in the device and, upon interface with a computer workstation 42, can increase the accuracy of the positioning, placement, display and synchronization of a displayed image.

Alternatively, passive trackers may be provided on the tracked tool for use with a passive position sensor system.

Multiple tracked tools, actively or passively tracked, may be used in conjunction with CAS, as may be supportable by the computer workstation 40.

Further, a plurality of additional positional trackers, active or passive, including clamps and pins, may be temporarily attached to various objects in the operating room for positioning and reference purposes, for example, on the patient's anatomy, on the patient table, and any other object in the operating room whose position is sought to be determined and displayed on the computer display 44 in CAS.

For image-guided use, data is transferred to the computer workstation 42 by the gravity sensor 56 and by the various optical sensors recording positional information for all optical trackers in the operating room, including the trackers on the tracking shield 48 on the image intensifier 36, the tracked instruments, and the trackers on the patient. Using the data obtained from the gravity sensor 54 and positional information of the image source 30 and image receptor 32 in correspondence with the degree of rotation of the imaging device 20, the positional distortion due to gravity induced C-arm bending is interpolated from the information previously stored in the LUT. Through use of software applications and mathematical modelling, including the use of the mathematical modelling associated with the calibration plate grid, the distortion in the image is computed and removed from the displayed image.

The software program stores LUT information in a file defined during the calibration process pre-operatively, including prior to surgery. The relationship between gravity (a vector defined by two angles) and the 3D position of the imaging source is modelled by a bi-cubic polynomial function. The relationship between magnetic north (vector defined by two angles) and image distortions is defined by at least a third degree polynomial function. The program calculates for each C-arm position the calculated image distortion and X-ray source positions are used to update the projection model (camera model) to allow graphical display of surgical tools on the images.

Figure 3:
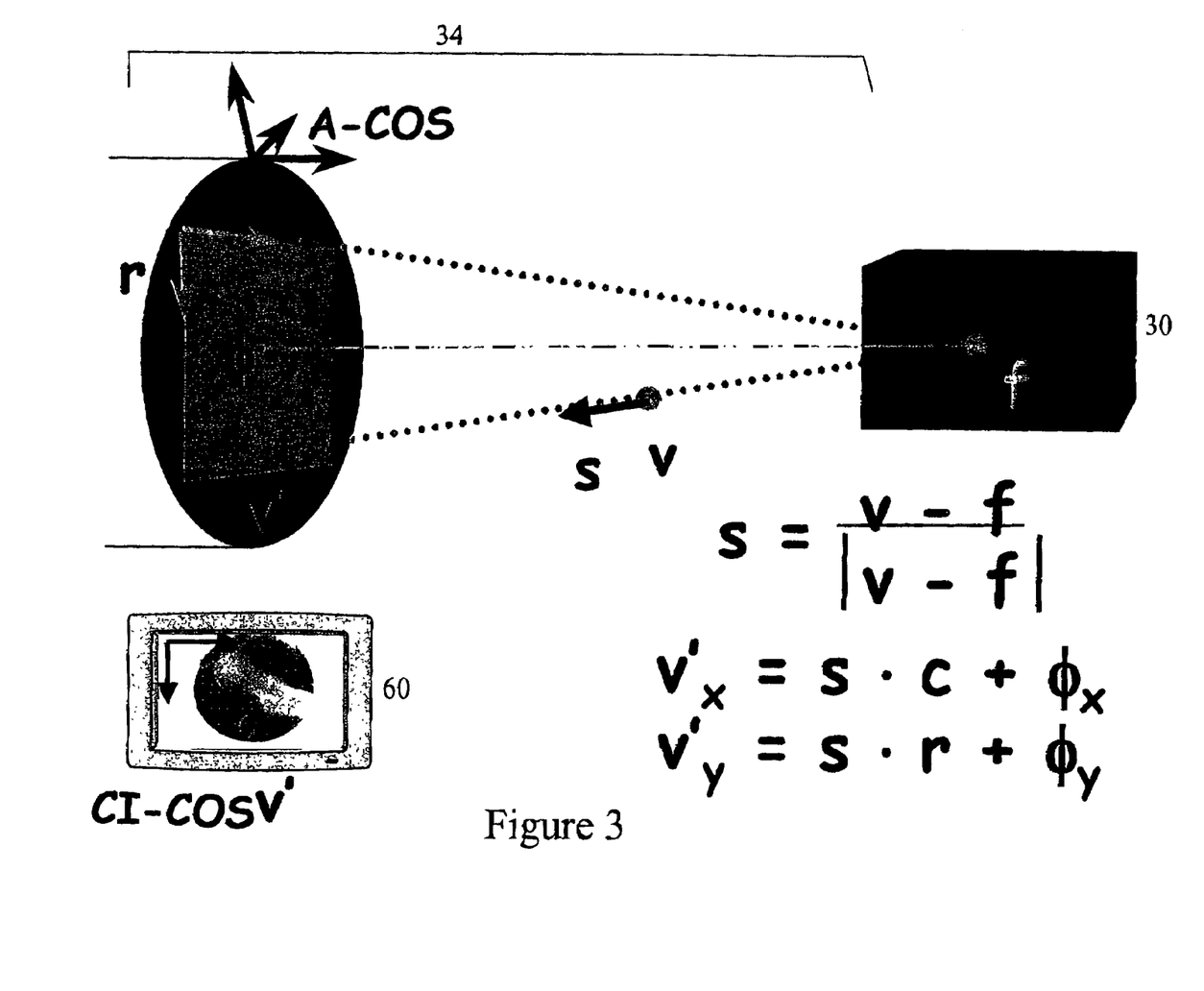
FIG. 3 illustrates a projection model used with an embodiment of the invention.

For example, a projection model as follows may be used to map the position and orientation of the tracked surgical tool in an acquired fluoroscopic image. FIG. 3 provides a sample projection model using the LUT from the calibration procedure. In FIG. 3, s is the direction vector of X-rays emanating from the X-ray source 30, f refers to the focal point of the X-ray source 30, v is a point in the free space 34, $v^1$ is a point in the image 60, c and r are co-ordinate vectors of an imaging plane, and ϕ is the piercing point. For a given point v in the space through which X-rays are passed, its image $v^1$ is subjected to a mathematical translation in which its x component ($v^1_x$) and y component ($v^1_y$) are computed and displayed as follows:

$$s = \frac{v-f}{|v-f|}$$
$$v'_x = s \cdot c + \phi_x$$
$$v'_y = s \cdot r + \phi_y$$

In a similar fashion, the imaging device 20 of the embodiment of FIG. 2 is used in image-guided surgery. The embodiment of FIG. 2 lacks a calibration plate on the C-arm 22, but is instead provided with a magnetic north sensor 56 on the support base 24 of the imaging device 20. For intra-operative use, data from the magnetic north sensor 58 is transferred to the computer workstation 42 in addition to the data from the gravity sensor 56 and from the various optical sensors recording positional information for all optical trackers in the operating room. The data obtained from the magnetic north sensor 58 is used to interpolate magnetic field induced distortion, using the information previously stored in the LUT, at the same time distortion due to C-arm bending is interpolated using positional and gravitational data also stored in the LUT. Through use of software application and mathematical modelling, substantially all distortion in the image can be computed and removed from the displayed image.

As can be appreciated by persons skilled in the art, other reference coordinates may be selected and other distortion variables may be computed for use in the calibration process described. Also, the calibration process may be adapted for use with other non-fluoroscopic medical imaging devices.

Numerous modifications, variations, and adaptations may be made to the particular embodiments of the invention described above without departing from the scope of the invention, which are defined in the claims.

What is claimed is:

1. A method of calibrating a C-arm imaging device comprising the steps of:
   determining a position of an imaging source for each of a plurality of orientations of the C-arm, including determining a reference position of the imaging source for a reference orientation;
   determining a position of an imaging receptor for each of the plurality of orientations, including determining a reference position of the imaging receptor for the reference orientation;
   determining a local gravity vector for each of the plurality of orientations;
   determining an imaging source focal point displacement due to bending for each of the plurality of orientations using the reference position of the imaging source, the reference position of the imaging receptor, the position of the imaging source and the position of the imaging receptor in correspondence to the local gravity vector; and
   storing information on the position of the imaging source, the position of the imaging receptor, the gravity vector, and the imaging source focal point displacement for each of the plurality of orientations, for use in subsequent interpolation of imaging source focal point displacement based on a specific position of an imaging receptor and a specific local gravity vector.

2. A method of claim 1 wherein the plurality of orientations is obtained by rotating the C-arm about a plurality of angles around a first axis and a plurality of angles around a second axis.

3. A method of claim 2 wherein the plurality of angles are spaced 10 degrees apart.

4. A method of claim 3 wherein the plurality of orientations comprise about 100 or more orientations.

5. A method of claim 1, wherein the position of the imaging source is determined by obtaining a coordinate position in three dimensional space.

6. A method of claim 1, wherein the position of the imaging receptor is determined by obtaining a coordinate position in three dimensional space.

7. A method of claim 1 wherein the local gravity vector is determined with reference to a moveable part of the C-arm.

8. A method of claim 7 wherein the local gravity vector is determined by obtaining the angular displacement of the moveable part from alignment with the local gravitational field.

9. A method of claim 7 wherein the moveable part of the C-arm is the imaging receptor.

10. A method of claim 1 wherein the imaging source focal point displacement is determined in conjunction with reference coordinates for the imaging source.

11. A method of claim 10 wherein the imaging source focal point displacement is derived from the change in position of the imaging source from the reference coordinates for the imaging source.

12. A method of claim 1 wherein the step of storing comprises saving information in a look-up table.

13. A method of claim 1 further comprising the steps of:
   determining a specific position of the imaging receptor;
   determining a specific gravity vector; and
   interpolating imaging source focal point displacement using the stored information.

14. A method of claim 1 further comprising the steps of:
   determining a magnetic field distortion for each of the plurality of orientations; and
   storing the magnetic field distortion for use in subsequent interpolation of magnetic field distortion based on a specific orientation of the C-arm.

15. A method of claim 14 wherein magnetic field distortion is determined by:
   determining a reference magnetic field vector in alignment with a magnetic pole for a reference orientation of the C-arm;
   determining a magnetic field vector for each of the plurality of orientations; and
   determining a change in magnetic field vector from the reference magnetic field vector for each of the plurality of orientations.

16. A method of claim 15 wherein the reference magnetic field vector, the magnetic field vector for each of the plurality of orientations, and the change in magnetic field vectors are expressed in coordinate form.

17. A method of claim 1 further comprising the step of using the interpolation of imaging source focal point displacement for projecting the position of a tracked object in computer assisted surgical systems.

18. A method of claim 14 further comprising the step of using the interpolation of magnetic field distortion for projecting the position of a tracked object in computer assisted surgical systems.

19. An apparatus for calibrating a C-arm imaging device comprising:
   a position determining module including:
      a first position tracker attached to an imaging source for determining a position of the imaging source for each of a plurality of orientations of the C-arm, including determining a reference position of the imaging source for a reference orientation;
      a second position tracker attached to an imaging receptor for determining a position of the imaging receptor for each of the plurality of orientations, including determining a reference position of the imaging receptor for the reference orientation;
   a gravity sensor attached to a mobile part of the C-arm for determining a local gravity vector for each of the plurality of orientations;
   a processing module for determining an imaging source focal point displacement due to bending for each of the plurality of orientations using the reference position of the imaging source, the reference position of the imaging receptor, the position of the imaging source and the position of the imaging receptor in correspondence to the local gravity vector; and
   a database module for storing information on the position of the imaging source, the position of the imaging receptor, the gravity vector, and the imaging source focal point displacement for each of the plurality of orientations, for use in subsequent interpolation of imaging source focal point displacement based on a specific position of an imaging receptor and a specific local gravity vector.

20. An apparatus of claim 19 wherein the position determining module comprises a position sensor which communicates with the first and second position trackers for computing the positions of the first and second position trackers.

21. An apparatus of claim 20 wherein the imaging source is an X-ray source.

22. An apparatus of claim 19 wherein the imaging source comprises an image intensifier.

23. An apparatus of claim 19 wherein the gravity sensor is positioned proximate to the imaging receptor.

24. An apparatus of claim 19 further comprising a sensor for determining a magnetic field distortion for each of the plurality of orientations.

25. An apparatus of claim 24 wherein the sensor for determining a magnetic field distortion comprises a magnetic pole sensor positioned proximate to the C-arm.

26. An apparatus of claim 25 wherein the magnetic pole sensor is positioned on a support base of the C-arm.

27. An apparatus of claim 25 wherein the C-arm lacks a calibration plate or dewarp grid.

28. An apparatus of claim 19 wherein the C-arm is provided with a single calibration plate.

29. An imaging system comprising:

a C-arm imaging device for obtaining image; and a system for calibrating the C-arm imaging device according to claim 19.

30. An imaging system comprising:

a C-arm imaging device for obtaining image; and a system for calibrating the C-arm imaging device according to claim 24.

* * * * *